(12) United States Patent
Fonte et al.

(10) Patent No.: US 9,585,623 B2
(45) Date of Patent: Mar. 7, 2017

(54) SYSTEMS AND METHODS FOR NUMERICALLY EVALUATING VASCULATURE

(71) Applicant: HeartFlow, Inc., Redwood City, CA (US)

(72) Inventors: Timothy A. Fonte, San Francisco, CA (US); Gilwoo Choi, Mountain View, CA (US); Jonathan Tang, Redwood City, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 14/254,621

(22) Filed: Apr. 16, 2014

(65) Prior Publication Data

US 2014/0303495 A1   Oct. 9, 2014

Related U.S. Application Data

(63) Continuation of application No. 13/656,183, filed on Oct. 19, 2012.

(51) Int. Cl.
*A61B 6/02* (2006.01)
*A61B 6/03* (2006.01)
(Continued)

(52) U.S. Cl.
CPC ............. *A61B 6/032* (2013.01); *A61B 5/026* (2013.01); *A61B 5/02007* (2013.01);
(Continued)

(58) Field of Classification Search
CPC ... A61B 5/02007; A61B 5/02755; A61B 6/03; A61B 6/00; A61B 6/507;
(Continued)

(56) References Cited

U.S. PATENT DOCUMENTS

2010/0076296 A1   3/2010 Mittal
2011/0206247 A1   8/2011 Dachille et al.
(Continued)

FOREIGN PATENT DOCUMENTS

| JP | 2007-505645 | 3/2007 |
| JP | 2008-525126 | 7/2008 |
| JP | 2009-542332 | 12/2009 |

OTHER PUBLICATIONS

Stahil, et al., "Coronary Computed Tomography Angiography Indicates Complexity of Percutaneous Coronary Interventions," Apr. 26, 2012, J Invasive Cardiol., 24(5) 196-201.*
(Continued)

*Primary Examiner* — Navin Natnithithadha
*Assistant Examiner* — Eric Messersmith
(74) *Attorney, Agent, or Firm* — Bookoff McAndrews, PLLC

(57) ABSTRACT

Systems and methods are disclosed for providing a cardiovascular score for a patient. A method includes receiving, using at least one computer system, patient-specific data regarding a geometry of multiple coronary arteries of the patient; and creating, using at least one computer system, a three-dimensional model representing at least portions of the multiple coronary arteries based on the patient-specific data. The method also includes evaluating, using at least one computer system, multiple characteristics of at least some of the coronary arteries represented by the model; and generating, using at least one computer system, the cardiovascular score based on the evaluation of the multiple characteristics. Another method includes generating the cardiovascular score based on evaluated multiple characteristics for portions of the coronary arteries having fractional flow reserve values of at least a predetermined threshold value.

20 Claims, 5 Drawing Sheets

(51) Int. Cl.
| | |
|---|---|
| *G06F 19/00* | (2011.01) |
| *A61B 5/02* | (2006.01) |
| *A61B 5/026* | (2006.01) |
| *G06T 19/00* | (2011.01) |
| A61B 6/00 | (2006.01) |
| A61B 8/08 | (2006.01) |
| A61B 5/055 | (2006.01) |

(52) U.S. Cl.
CPC .............. *A61B 6/481* (2013.01); *A61B 6/507* (2013.01); *A61B 6/5205* (2013.01); *G06F 19/3437* (2013.01); *G06T 19/00* (2013.01); A61B 5/055 (2013.01); A61B 6/504 (2013.01); A61B 8/0891 (2013.01); A61B 2576/023 (2013.01); G06F 19/3431 (2013.01); G06T 2210/41 (2013.01)

(58) Field of Classification Search
CPC ....... A61B 6/5205; A61B 5/026; A61B 6/032; A61B 6/481; A61B 8/0891; A61B 5/055; A61B 6/504; A61B 2576/023; G06T 19/00; G06T 2210/41; G06F 19/3437; G06F 19/3431
USPC .......................................... 600/481–484, 504
See application file for complete search history.

(56) References Cited

U.S. PATENT DOCUMENTS

| | | |
|---|---|---|
| 2011/0295579 A1 | 12/2011 | Tang et al. |
| 2012/0041318 A1 | 2/2012 | Taylor |
| 2012/0041323 A1* | 2/2012 | Taylor et al. ................ 600/508 |
| 2012/0243761 A1 | 9/2012 | Senzig et al. |

OTHER PUBLICATIONS

International Search Report issued in corresponding International Application No. PCT/US2013/065495, mailed Feb. 7, 2014.
International Preliminary Report on Patentability mailed on Apr. 21, 2015, in corresponding International PCT Patent Application No. PCT/US2013/065495, filed on Oct. 17, 2013 (7 pages).
Patent Examination Report No. 1 mailed on Apr. 29, 2015, in corresponding Australian Patent Application No. 2013331213, filed on Apr. 17, 2015 (3 pages).
Patent Examination Report No. 2 mailed on Jul. 31, 2015, in corresponding Australian Patent Application No. 2013331213, filed on Apr. 17, 2015 (3 pages).
Patent Examination Report No. 3 mailed on Jan. 28, 2016, in corresponding Australian Patent Application No. 2013331213, filed on Apr. 17, 2015 (3 pages).
Examiner's Report mailed on Jul. 15, 2015, in corresponding Canadian Patent Application No. 2,888,098, filed on Apr. 9, 2015 (4 pages).
English-language translation of Notice of Preliminary Rejection mailed on Sep. 11, 2015, in corresponding Korean Patent Application No. 10-2015-7011241, filed on Apr. 29, 2015 (4 pages).
English-language translation of Notice of Final Rejection mailed on Jan. 6, 2016, in corresponding Korean Patent Application No. 10-2015-7011241, filed on Apr. 29, 2015 (2 pages).
Sianos et al., "The SYNTAX Score: an angiographic tool grading the complexity of coronary artery disease", 2005, pp. 219-227, vol. 1, EuroIntervention (9 pages).
Serruys et al., "Percutaneous Coronary Intervention versus Coronary-Artery Bypasss Grafting for Severe Coronary Artery Disease", Mar. 5, 2009, pp. 961-972, vol. 360, No. 10, The New England Journal of Medicine (12 pages).
English-language translation of Notice of Rejection mailed on May 30, 2016, in corresponding Japanese Patent Application No. 2015-537831, filed Oct. 17, 2013 (6 pages).

* cited by examiner

SYSTEMS AND METHODS FOR NUMERICALLY EVALUATING VASCULATURE

CROSS REFERENCE TO RELATED APPLICATIONS

This application is a continuation of U.S. patent application Ser. No. 13/656,183, filed on Oct. 19, 2012, the entirety of which is hereby incorporated herein by reference.

TECHNICAL FIELD

Embodiments of the present disclosure include systems and methods for numerically evaluating vasculature, such as scoring coronary vasculature by modeling coronary anatomy. More particularly, embodiments are directed to systems and methods for patient-specific scoring of coronary vasculature based on coronary anatomy and optionally also on fractional flow reserve or other functional metrics values calculated from computerized modeling of blood flow.

BACKGROUND

Coronary artery disease may produce coronary lesions in the blood vessels providing blood to the heart, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it cannot be used to predict changes in coronary blood flow, pressure, or myocardial perfusion under other physiologic states, e.g., exercise, nor can it be used to predict outcomes of interventions.

Thus, patients may also require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to what has been referred to as an "oculostenotic reflex" of some interventional cardiologists to insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of maximally increased coronary blood flow, e.g., induced by intravenous administration of adenosine. The blood pressures may be measured by inserting a pressure wire into the patient. Thus, the decision to treat a lesion based on the determined FFR may be made after the initial cost and risk of diagnostic cardiac catheterization has already been incurred.

Another technique for evaluating a patient's coronary vasculature is the SYNTAX scoring system and method, which is a technique to score the complexity and severity of coronary artery disease. The SYNTAX score is a rating method used to help determine whether patients should be treated with percutaneous coronary intervention (PCI) or coronary artery bypass graft (CABG). Standard SYNTAX scoring is performed by evaluating a patient's coronary anatomy via angiograms, answering a series of questions, and assigning point values based on the answers to the questions. For example, a cardiologist may review a patient's angiogram and assign penalty points for lesions based on, for example, each lesion's type, shape, and location in the patient's coronary tree. The assessed points are then added together to output a single SYNTAX score for the patient. In one exemplary embodiment, if the score is less than 34, PCI is appropriate, and if the score is greater than 34, then CABG will more likely produce a better outcome. It has been found that SYNTAX scoring is very effective in evaluating the complexity and extent of disease in a patient's coronary vasculature, and identifying the most appropriate intervention (e.g., PCI vs. CABG). An embodiment of the SYNTAX scoring system is operating at http://www.syntaxscore.com/, which includes a scoring tutorial, vessel segment definitions, and scoring calculator, the entire disclosure of which is incorporated herein by reference.

Despite its significant benefits, SYNTAX scoring is traditionally an invasive technique because it is performed based on angiograms. Moreover, SYNTAX scoring can be a very time consuming process, as it requires cardiologists to manually/visually evaluate angiograms, answer a long series of questions, and assign a score based on each answer. In addition, the results of SYNTAX scoring are cardiologist-dependent, and may vary somewhat based on how one cardiologist perceives and/or scores angiogram images compared to how other cardiologists do so. For this reason, SYNTAX scoring is sometimes performed by several cardiologists, e.g. a three-person panel, so as to generate an average SYNTAX score. However, such a protocol further increases the man-hours involved in generating a useable SYNTAX score. Finally, traditional SYNTAX scoring is usually performed based on a patient's entire coronary vasculature, without regard to any calculated functional result of an identified lesion. For example, a cardiologist may include in a SYNTAX score penalty points for a lesion that does not negatively impact downstream FFR.

Thus, a need exists for systems and methods for assessing coronary anatomy, coronary artery disease, myocardial perfusion, and coronary artery flow noninvasively. In addition, a need exists for noninvasively evaluating the complexity and extent of disease in a patient's coronary vasculature, and identifying the most appropriate intervention (e.g., PCI vs. CABG). In addition, a need exists for evaluating the complexity and extent of disease in a patient's coronary vasculature by automatically performing a numerical evaluation based on noninvasively obtained patient-specific data. A need also exists for systems and methods that incorporate the functional impact of lesions, e.g. based on noninvasive FFR calculation, when performing numerical evaluation of a patient's coronary vasculature.

The foregoing general description and the following detailed description are exemplary and explanatory only and are not restrictive of the disclosure.

SUMMARY

In accordance with an embodiment, a method is disclosed for providing a cardiovascular score for a patient. The method includes receiving, using at least one computer system, patient-specific data regarding a geometry of multiple coronary arteries of the patient; and creating, using at least one computer system, a three-dimensional model representing at least portions of the multiple coronary arteries based on the patient-specific data. The method also includes evaluating, using at least one computer system, multiple characteristics of at least some of the coronary arteries represented by the model; and generating, using at least one computer system, the cardiovascular score based on the evaluation of the multiple characteristics.

In accordance with another embodiment, a computer-implemented method is disclosed for generating a cardiovascular score for a patient. The method includes: receiving patient-specific data regarding a geometry of multiple coronary arteries of the patient, and creating a model representing at least portions of the multiple coronary arteries based on the patient-specific data. The method further includes: evaluating a plurality of characteristics of at least portions of the coronary arteries represented on the three-dimensional model; assigning numerical values to the plurality of characteristics based on the evaluation of each of the plurality of characteristics; and generating the cardiovascular score as a function of the assessed numerical values.

In accordance with another embodiment, a method is disclosed for providing a cardiovascular score for a patient. The method includes: receiving, using at least one computer system, patient-specific data regarding a geometry of multiple coronary arteries of the patient; and creating, using at least one computer system, a three-dimensional model representing at least portions of the multiple coronary arteries based on the patient-specific data. The method further includes: calculating, using at least one computer system, fractional flow reserve values at a plurality of locations of the at least portions of the coronary arteries; evaluating, using at least one computer system, multiple characteristics of at least portions of the coronary arteries represented by the model; and generating, using at least one computer system, the cardiovascular score based on the evaluated multiple characteristics for portions of the coronary arteries having fractional flow reserve values of at least a predetermined threshold value.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

DESCRIPTION OF THE EMBODIMENTS

Reference will now be made in detail to exemplary embodiments, examples of which are illustrated in the accompanying drawings. Wherever possible, the same reference numbers will be used throughout the drawings to refer to the same or like parts.

In general, the present disclosure relates to performing a numerical evaluation of a patient's coronary vasculature (e.g., by scoring the coronary arterial vasculature of the patient), based on analysis of a patient's anatomical coronary model and, optionally, various calculated data relating to blood flow in a specific patient. In one embodiment, the disclosure relates to systems and methods for assessing coronary anatomy, coronary artery disease, myocardial perfusion, and coronary artery flow noninvasively. The presently disclosed systems and methods assist cardiologists in evaluating the complexity and extent of disease in a patient's coronary vasculature, and identifying the most appropriate intervention (e.g., PCI vs. CABG). Accordingly, systems and methods are disclosed for evaluating the complexity and extent of disease in a patient's coronary vasculature by automatically performing a numerical evaluation of noninvasively obtained patient-specific data. Moreover, systems and methods are disclosed for incorporating the functional impact of lesions, e.g. based on noninvasive FFR calculation, when performing numerical evaluation of a patient's coronary vasculature. Such systems and methods may benefit cardiologists who diagnose and plan treatments for patients with suspected coronary artery disease.

In an exemplary embodiment, various information relating to blood flow in a specific patient (e.g., FFR values) is calculated using information retrieved from the patient noninvasively. Various embodiments of systems and methods for performing such calculations are described in greater detail in U.S. patent application Ser. No. 13/013,561, filed Jan. 25, 2011, and entitled "Method and System for Patient-Specific Modeling of Blood Flow," which is assigned to the assignee of the present application and which is hereby incorporated by reference in its entirety.

Figure 1:
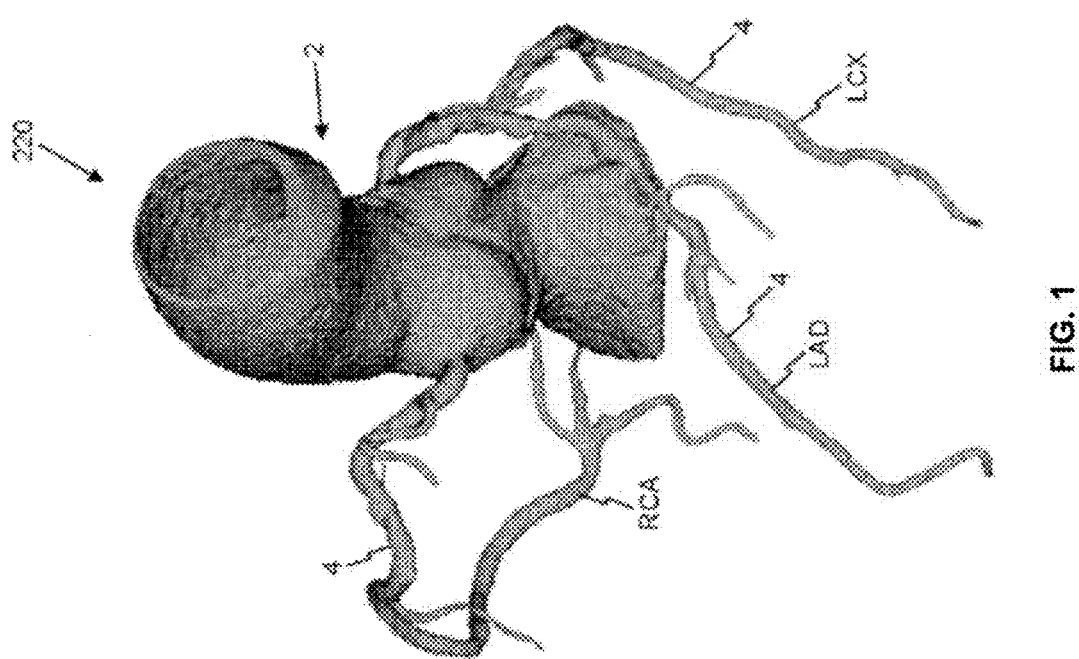
FIG. 1 shows an exemplary three-dimensional model of a patient's coronary vasculature, generated using noninvasively obtained imaging data.

In some embodiments, the information determined by the disclosed systems and methods may relate to blood flow in the patient's coronary vasculature. Alternatively, the determined information may relate to blood flow in other areas of the patient's vasculature, such as carotid, peripheral, abdominal, renal, and cerebral vasculature. The coronary vasculature includes a complex network of vessels ranging from large arteries to arterioles, capillaries, venules, veins, etc. FIG. 1 depicts a model 220 of a portion of the coronary vasculature that circulates blood to and within the heart and includes an aorta 2 that supplies blood to a plurality of main coronary arteries 4 (e.g., the left anterior descending (LAD) artery, the left circumflex (LCX) artery, the right coronary (RCA) artery, etc.), which may further divide into branches of arteries or other types of vessels downstream from the aorta 2 and the main coronary arteries 4. Thus, the exemplary systems and methods may determine various information relating to blood flow within the aorta, the main coronary arteries, and/or other coronary arteries or vessels downstream from the main coronary arteries. Although the aorta and coronary arteries (and the branches that extend therefrom) are discussed below, the disclosed systems and methods may also apply to other types of vessels.

In an exemplary embodiment, the information determined by the disclosed systems and methods may include, but is not limited to, various blood flow characteristics or parameters, such as blood flow velocity, pressure (or a ratio thereof), flow rate, and FFR at various locations in the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision of whether and how to treat a lesion may be made without the cost and risk associated with invasive procedures.

Figure 2:
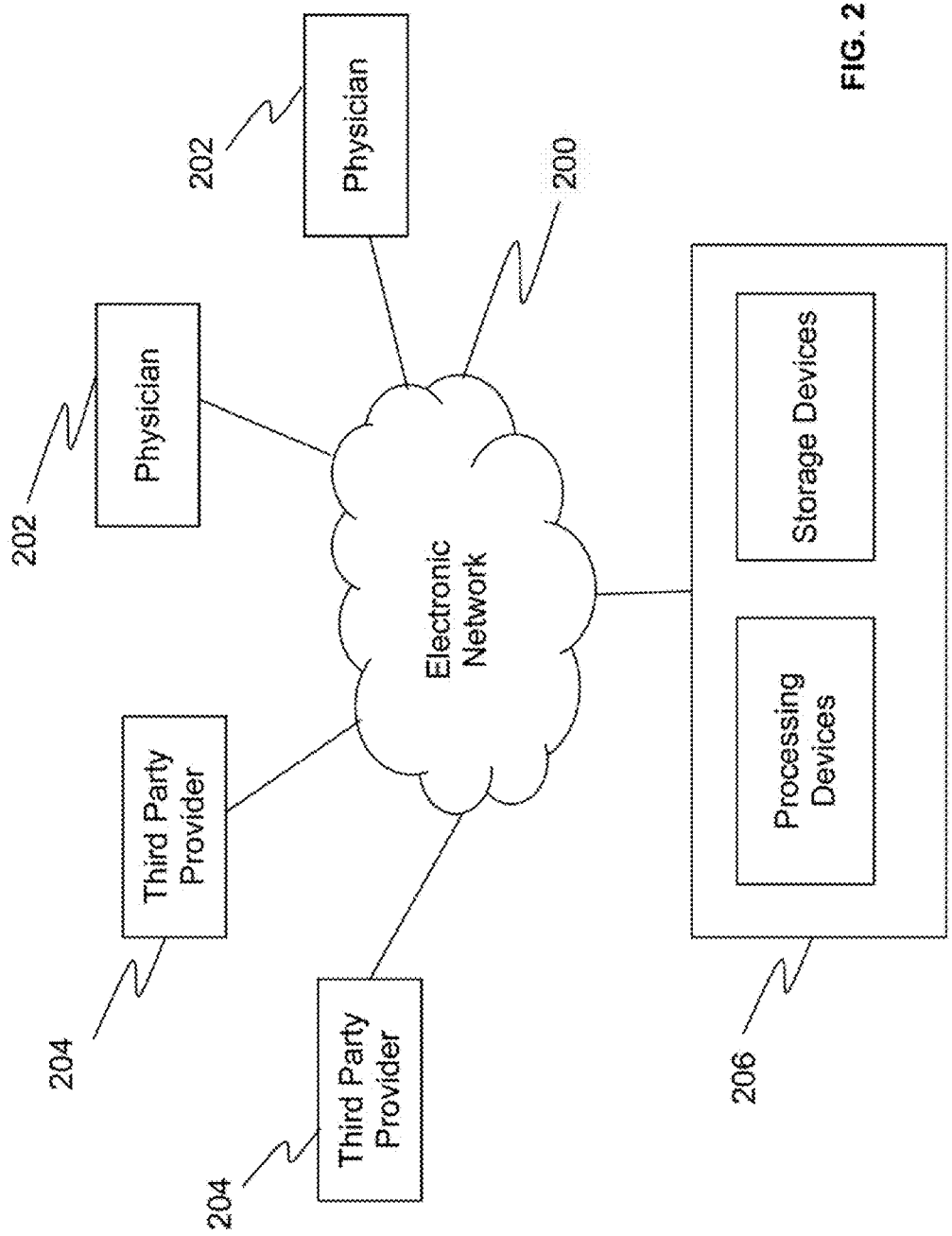
FIG. 2 is a block diagram of an exemplary system and network for scoring patient coronary vasculature, according to embodiments of the present disclosure.

FIG. 2 depicts a block diagram of an exemplary system and network for scoring a patient's coronary vasculature from vessel geometry, physiological information, and/or blood flow information. Specifically, FIG. 2 depicts a plurality of physicians 202 and third party providers 204, any of whom may be connected to an electronic network 200, such as the Internet, through one or more computers, servers, and/or handheld mobile devices. Physicians 202 and/or third party providers 204 may create or otherwise obtain images of one or more patients' cardiac and/or vascular systems, as will be described below with respect to FIG. 3. The physicians 202 and/or third party providers 204 may also obtain any combination of patient-specific information, such as age, medical history, blood pressure, blood viscosity, etc. Physicians 202 and/or third party providers 204 may transmit the cardiac/vascular images and/or patient-specific information to computing system 206 over the electronic network 200. Computing system 206 may include storage devices for storing images and data received from physicians 202 and/or third party providers 204. Computing system 206 may also include processing devices for processing images and data stored in the storage devices, according to methods disclosed herein.

Figure 3:
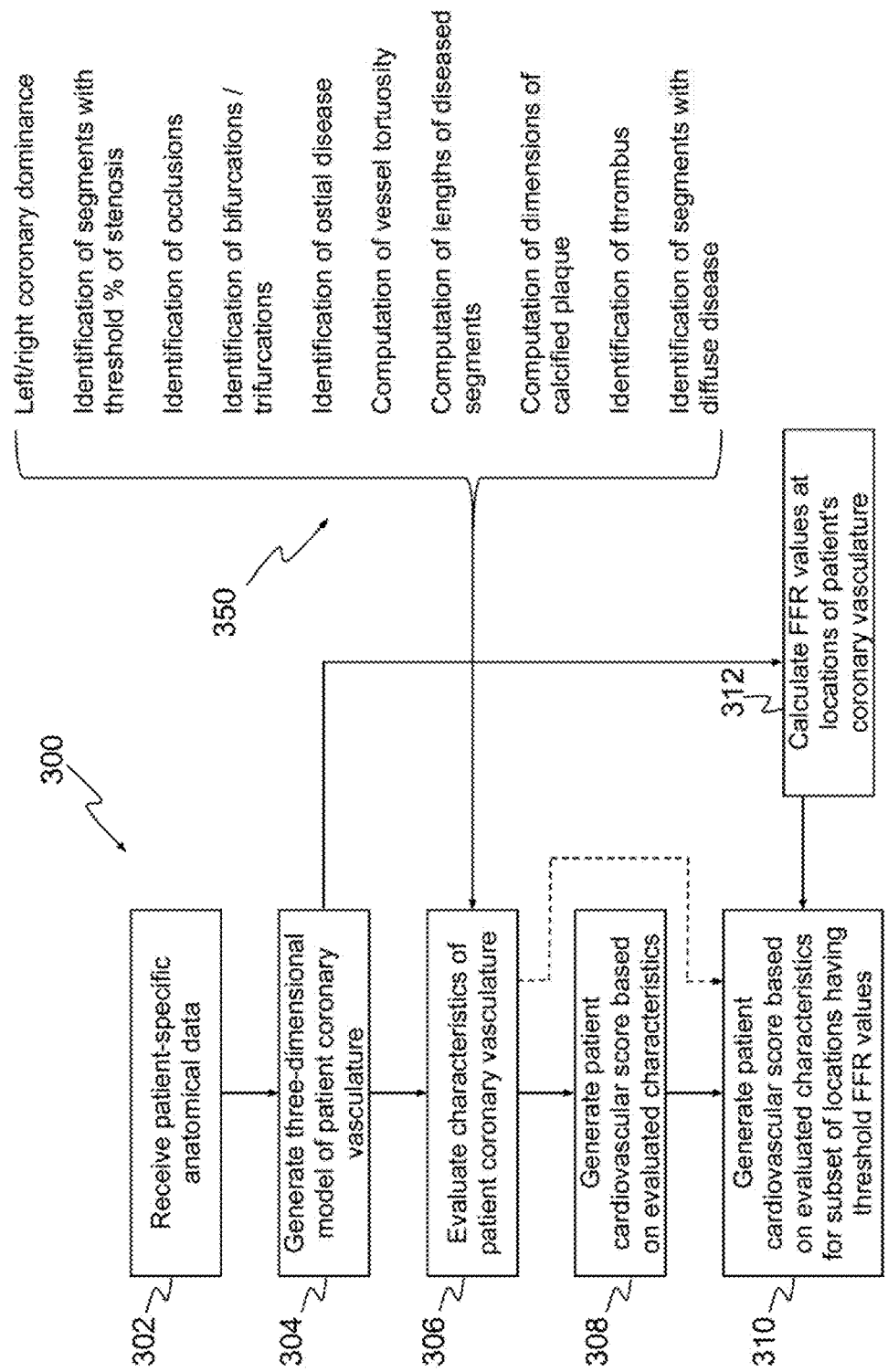
FIG. 3 is a flow chart of an exemplary method for scoring patient coronary vasculature, according to embodiments of the present disclosure.

FIG. 3 is a block diagram of an exemplary method 300 for numerically evaluating, i.e., scoring, patient coronary vasculature from models of vessel geometry, physiological information, and/or blood flow information, according to an exemplary embodiment of the present disclosure. More specifically, method 300 involves noninvasively evaluating the complexity and extent of disease in a patient's coronary vasculature, and identifying the most appropriate intervention (e.g., PCI vs. CABG). In one embodiment, method 300 incorporates the functional impact of lesions, e.g. based on noninvasive FFR calculation, when performing numerical evaluation of a patient's coronary vasculature. In one embodiment, the method of FIG. 3 may be performed by computing system 206, based on information received from physicians 202 and/or third party providers 204 over electronic network 200.

As shown in FIG. 3, method 300 may include receiving patient-specific anatomical data (step 302). For example, information regarding the patient's anatomy (e.g., at least a portion of the aorta and a proximal portion of the main coronary arteries (and the branches extending therefrom) connected to the aorta), may be received and preprocessed. The patient-specific anatomical data may be obtained noninvasively, e.g., by CCTA, as will be described below.

In one embodiment, step 302 may include initially selecting a patient. For example, the patient may be selected by the physician when the physician determines that information about the patient's coronary blood flow is desired, e.g., if the patient is experiencing symptoms associated with coronary artery disease, such as chest pain, heart attack, etc.

Patient-specific anatomical data may include data regarding the geometry of the patient's heart, e.g., at least a portion of the patient's aorta, a proximal portion of the main coronary arteries (and the branches extending therefrom) connected to the aorta, and the myocardium. The patient-specific anatomical data may be obtained noninvasively, e.g., using a noninvasive imaging method. For example, CCTA is an imaging method in which a user may operate a computer tomography (CT) scanner to view and create images of structures, e.g., the myocardium, the aorta, the main coronary arteries, and other blood vessels connected thereto. The CCTA data may be time-varying, e.g., to show changes in vessel shape over a cardiac cycle. CCTA may be used to produce an image of the patient's heart. For example, 64-slice CCTA data may be obtained, e.g., data relating to slices of the patient's heart, and assembled into a three-dimensional image.

Alternatively, other noninvasive imaging methods, such as magnetic resonance imaging (MRI) or ultrasound (US), or invasive imaging methods, such as digital subtraction angiography (DSA), may be used to produce images of the structures of the patient's anatomy. The imaging methods may involve injecting the patient intravenously with a contrast agent to enable identification of the structures of the anatomy. The resulting imaging data (e.g., provided by CCTA, MRI, etc.) may be provided by a third-party vendor, such as a radiology lab or a cardiologist, by the patient's physician, etc.

Other patient-specific anatomical data may also be determined from the patient noninvasively. For example, physiological data such as the patient's blood pressure, baseline heart rate, height, weight, hematocrit, stroke volume, etc., may be measured. The blood pressure may be the blood pressure in the patient's brachial artery (e.g., using a pressure cuff), such as the maximum (systolic) and minimum (diastolic) pressures.

The patient-specific anatomical data obtained as described above may be transferred over a secure communication line (e.g., via a network 200). For example, the data may be transferred to a server or other computer system 206 for performing the computational analysis. In an exemplary embodiment, the data may be transferred to a server or other computer system operated by a service provider providing a web-based service. Alternatively, the data may be transferred to a computer system operated by the patient's physician or other user. The transferred data may be reviewed to determine if the data is acceptable. The determination may be performed by the user and/or by the computer system. For example, the transferred data (e.g., the CCTA data and other data) may be verified by a user and/or by the computer system, e.g., to determine if the CCTA data is complete (e.g., includes sufficient portions of the aorta and the main coronary arteries) and corresponds to the correct patient.

The transferred data (e.g., the CCTA data and other data) may also be preprocessed and assessed. The preprocessing and/or assessment may be performed by a user and/or by the computer system and may include, e.g., checking for misregistration, inconsistencies, or blurring in the CCTA data, checking for stents shown in the CCTA data, checking for other artifacts that may prevent the visibility of lumens of the blood vessels, checking for sufficient contrast between the structures (e.g., the aorta, the main coronary arteries, and other blood vessels) and the other portions of the patient, etc.

The transferred data may be evaluated to determine if the data is acceptable based on the verification, preprocessing, and/or assessment described above. During the verification, preprocessing, and/or assessment described above, the user and/or computer system may be able to correct certain errors or problems with the data. If, however, there are too many errors or problems, then the data may be determined to be unacceptable, and the user and/or computer system may generate a rejection report explaining the errors or problems necessitating the rejection of the transferred data. Optionally, a new CCTA scan may be performed and/or the physiological data described above may be measured from the patient again. If the transferred data is determined to be acceptable, then the method may proceed to step 304 for generation of a three-dimensional model, as described below.

As shown in FIG. 3, method 300 may then include generating a three-dimensional model of the patient's anatomy, based on the obtained patient-specific anatomical data (step 304). It will be appreciated that as an alternative embodiment, a lower dimensional model may be used, such as a one-dimensional model of the vessels combined with an algorithm that encodes vessel sizes along their lengths.

According to one embodiment, the three-dimensional model of the coronary vessels may be generated using the received CCTA data. FIG. 1 shows an example of the surface of a three-dimensional model 220 generated using the CCTA data. For example, the model 220 may include, e.g., at least a portion of the aorta, at least a proximal portion of one or more main coronary arteries connected to that portion of the aorta, at least a proximal portion of one or more branches connected to the main coronary arteries, etc. The modeled portions of the aorta, the main coronary arteries, and/or the branches may be interconnected and treelike such that no portion is disconnected from the rest of the model 220. The process of generating the model 220 may be referred to as segmentation.

In one embodiment, computer system 206 may automatically segment at least a portion of the aorta and the myocardium (or other heart tissue, or other tissue connected to the arteries to be modeled). The myocardium or other tissue may also be segmented based on the CCTA data received in step 302. For example, the computer system may display to the user the three-dimensional image or slices thereof produced from the CCTA data. The computer system may also segment at least a portion of the main coronary arteries connected to the aorta. In an exemplary embodiment, the computer system may allow the user to select one or more coronary artery root or starting points in order to segment the main coronary arteries.

Segmentation may be performed using various methods. In one embodiment, segmentation is performed based on threshold-based segmentation, edge-based segmentation, graph theory, machine-learning methods, or a combination of those methods. Segmentation may be performed automatically by the computer system based on user inputs or without user inputs. For example, in an exemplary embodiment, the user may provide inputs to the computer system in order to generate a first initial model. The three-dimensional image may include portions of varying intensity of lightness. For example, lighter areas may indicate the lumens of the aorta, the main coronary arteries, and/or the branches. Darker areas may indicate the myocardium and other tissue of the patient's heart. The locations of the surfaces may be determined based on the contrast (e.g., relative darkness and lightness) and shape of the myocardium compared to other structures of the heart in the CCTA data. Thus, the geometry of the myocardium may be determined. For example, the CCTA data may be analyzed to determine the location of the internal and external surfaces of the myocardium, e.g., the left and/or right ventricles.

The segmentation of the aorta, the myocardium, and/or the main coronary arteries may be reviewed and/or corrected, if necessary. The review and/or correction may be performed by the computer system and/or the user. For example, in an exemplary embodiment, the computer system may automatically review the segmentation, and the user may manually correct the segmentation if there are any errors, e.g., if any portions of the aorta, the myocardium, and/or the main coronary arteries in the model 220 are missing or inaccurate. Generation of the three-dimensional model may further involve identifying or generating one or more of the following properties of the patient's anatomy based on the three-dimensional model.

In one embodiment, the myocardial mass may be calculated, e.g., by the computer system analyzing model 220. For example, the myocardial volume may be calculated based on the locations of the surfaces of the myocardium determined as described above, and the calculated myocardial volume may be multiplied by the density of the myocardium to calculate the myocardial mass. The density of the myocardium may be preset or calculated.

In one embodiment, the centerlines of the various vessels (e.g., the aorta, the main coronary arteries, etc.) of the model 220 may also be determined, e.g., by the computer system. In an exemplary embodiment, the determination may be performed automatically by the computer system analyzing surfaces, shape, and contrast in the model 220. The centerlines may be reviewed and/or corrected, if necessary, either by the computer system and/or the user. For example, in an exemplary embodiment, the computer system may automatically review the centerlines, and the user may manually correct the centerlines if there are any errors, e.g., if any centerlines are missing or inaccurate.

In one embodiment, calcium or plaque (causing narrowing of a vessel) may be detected, e.g., by the computer system. In an exemplary embodiment, the computer system may automatically detect the plaque by analyzing surfaces and contrast in the model 220. For example, the plaque may be detected in the three-dimensional image and excluded from the model 220. The plaque may be identified in the three-dimensional image since the plaque appears as areas that are even brighter or darker than the lumens of the aorta, the main coronary arteries, and/or the branches. Thus, the plaque may be detected by the computer system as having an intensity value above or below a set value or may be detected visually by the user. Shape information, learning algorithms, and image analysis may also be used to detect and segment plaque. After detecting the plaque, the computer system may exclude the plaque from the model 220 so that the plaque is not considered as part of the lumen or open space in the vessels. Alternatively, the computer system may indicate the plaque on the model 220 using a different color, shading, or other visual indicator than the aorta, the main coronary arteries, and/or the branches.

In one embodiment, the detected plaque may be automatically segmented, e.g., by the computer system. For example, the plaque may be segmented based on the CCTA data. The CCTA data may be analyzed to locate the plaque (or a surface thereof) based on the contrast (e.g., relative darkness and lightness) of the plaque compared to other structures of the heart in the CCTA data. Thus, the geometry of the plaque may also be determined. The segmentation of the plaque may be reviewed and/or corrected, if necessary, either by the computer system and/or the user. For example, in an exemplary embodiment, the computer system may automatically review the segmentation, and the user may manually correct the segmentation if there are any errors, e.g., if any plaque is missing or shown inaccurately.

In one embodiment, the branches connected to the main coronary arteries may be automatically segmented, e.g., by the computer system. For example, the branches may be segmented using similar methods for segmenting the main coronary arteries. The computer system may also automatically segment the plaque in the segmented branches. Alternatively, the branches (and any plaque contained therein) may be segmented at the same time as the main coronary arteries. The segmentation of the branches may be reviewed and/or corrected, if necessary, either by the computer system and/or the user. For example, in an exemplary embodiment, the computer system may automatically review the segmentation, and the user may manually correct the segmentation if there are any errors, e.g., if any portions of the branches in the model 220 are missing or inaccurate.

In one embodiment, the computer system may segment branches of model 220 into one or more of the following defined segments, as defined at http://www.syntaxscore.com, as referenced above:

1 RCA proximal From ostium to one half the distance to the acute margin of the heart.
2 RCA mid From end of first segment to acute margin of heart.
3 RCA distal From the acute margin of the heart to the origin of the posterior descending artery.
4 Posterior descending Running in the posterior interventricular groove.
16 Posterolateral from RCA Posterolateral branch originating from the distal coronary artery distal to the crux.
16a Posterolateral from RCA First posterolateral branch from segment 16.
16b Posterolateral from RCA Second posterolateral branch from segment 16.
16c Posterolateral from RCA Third posterolateral branch from segment 16.
5 Left main From the ostium of the LCA through bifurcation into left anterior descending and left circumflex branches.
6 LAD proximal Proximal to and including first major septal branch.
7 LAD mid LAD immediately distal to origin of first septal branch and extending to the point where LAD forms an angle (RAO view). If this angle is not identifiable this segment ends at one half the distance from the first septal to the apex of the heart.
8 LAD apical Terminal portion of LAD, beginning at the end of previous segment and extending to or beyond the apex.
9 First diagonal The first diagonal originating from segment 6 or 7.
9a First diagonal a Additional first diagonal originating from segment 6 or 7, before segment 8.
10 Second diagonal Second diagonal originating from segment 8 or the transition between segment 7 and 8.
10a Second diagonal a Additional second diagonal originating from segment 8.
11 Proximal circumflex Main stem of circumflex from its origin of left main to and including origin of first obtuse marginal branch.
12 Intermediate/anterolateral Branch from trifurcating left main other than proximal LAD or LCX. Belongs to the circumflex territory.
12a Obtuse marginal a First side branch of circumflex running in general to the area of obtuse margin of the heart.
12b Obtuse marginal b Second additional branch of circumflex running in the same direction as 12.
13 Distal circumflex The stem of the circumflex distal to the origin of the most distal obtuse marginal branch and running along the posterior left atrioventricular grooves. Caliber may be small or artery absent.
14 Left posterolateral Running to the posterolateral surface of the left ventricle. May be absent or a division of obtuse marginal branch.
14a Left posterolateral a Distal from 14 and running in the same direction.
14b Left posterolateral b Distal from 14 and 14 a and running in the same direction.
15 Posterior descending Most distal part of dominant left circumflex when present. Gives origin to septal branches. When this artery is present, segment 4 is usually absent.

The model 220 may be corrected if any misregistration, stents, or other artifacts are located (e.g., during the review of the CCTA data), either by a user and/or by the computer system. For example, if a misregistration or other artifact (e.g., inconsistency, blurring, an artifact affecting lumen visibility, etc.) is located, the model 220 may be reviewed and/or corrected to avoid an artificial or false change in the cross-sectional area of a vessel (e.g., an artificial narrowing). If a stent is located, the model 220 may be reviewed and/or corrected to indicate the location of the stent and/or to correct the cross-sectional area of the vessel where the stent is located, e.g., based on the size of the stent.

If the segmentation of the model 220 is independently verified as acceptable, then, optionally, the model 220 may be output and smoothed. The smoothing may be performed by the user and/or by the computer system. For example, ridges, points, or other discontinuous portions may be smoothed. The model 220 may be output to a separate software module to be prepared for computational analysis, etc.

Once the three-dimensional model has been generated, method 300 may further include evaluating characteristics of the patient's coronary vasculature (step 306) based on analysis of the generated model. As shown in FIG. 3, evaluated characteristics of the patient's coronary vasculature may include one or more of the characteristics 350, including: (i) identification of left/right coronary dominance; (ii) identification of segments with threshold percentage of stenosis; (iii) identification of occlusions; (iv) identification of bifurcations/trifurcations; (v) identification of ostial disease; (vi) computation of vessel tortuosity; (vii) computation of lengths of diseased segments; (viii) computation of dimensions of calcified plaque; (ix) identification of thrombus, and/or (x) identification of segments with diffuse disease. Notwithstanding the exemplary identified characteristics 350, evaluation step 306 may include evaluating any other characteristic of patient coronary vasculature that is relevant to scoring an extent of cardiovascular complexity and/or disease.

In general, evaluation step 306 may include evaluating one or more of characteristics 350, and assessing one or more numerical values or "points" based on the evaluation of each characteristic. For example, in one embodiment, evaluation step 306 may involve determining whether the patient's left or right side of coronary vasculature is dominant. For example, computer system 206 may analyze model 220 to determine vessel sizes and topological structure, and process resulting data to identify the existence of either left or right dominance, if any. In one embodiment, computer system 206 may label the patient's posterior descending artery (PDA), trace the PDA back to the patient's ostium where it branches with either the left circumflex artery (LCX) (meaning the coronaries are left dominant) or the right coronary artery (RCA) (meaning the coronaries are right dominant). The computer system 206 may detect the PDA based on ventricular landmarks in model 220, and "vesselness response" (i.e., how similar a modeled shape appears to a typical vessel). Machine learning algorithms may also be used to compare the patient anatomy to a database of other patients to establish left/right dominance based on vessel sizes and position. In one embodiment, the computer system identifies dominance based on distal vessel size, whereby if distal RCA is less than 1.5 mm, or some other threshold compared to the LCX, then the patient is left dominant. Conversely, proximal RCA size of a predetermined size may be indicative of right hand dominance. The computer system 206 may then assign one or more points based on any left or right dominance, and/or an extent of any identified left or right dominance. Left and right dominance can be automatically determined on the basis of connectivity analysis of constructed coronary topology. For example, if the PDA is connected with RCA, then the system may be classified as right-dominant, whereas if the PDA is connected with circumflex artery, then the system may be classified as left-dominant.

The evaluation step 306 may also involve identifying segments with disease. For example, computer system 206 may analyze model 220 to determine which segments contain one or more lesions, e.g., based on identification of segments with some predetermined threshold percentage of stenosis. Computer system 206 may identify lesions based on image contrast, or any other suitable technique. In one embodiment, computer system 206 may identify segments as exhibiting stenosis if they have 50% or greater difference in contours compared to a vessel centerline. Stenotic lesions may be automatically identified by computing minima locations of a cross-sectional area curve along a centerline with numerical derivatives. The cross-sectional area curve may be smoothed (e.g., by Fourier smoothing) prior to performing a derivative operation in order to eliminate noise components in the area curve. The computer system may identify diseased segments by projecting identified plaque segmentation onto a vessel centerline. Machine learning may also be employed to compare sections that were labeled with plaque to a database of expert annotated data to determine a confidence in rating the stenosis as > or <50%. Computer system 206 may then assign one or more points based on any diseased segments. In one embodiment, points may be assessed based on how many lesions a given segment contains, the type of lesions identified, and/or the location or identity of the segment containing a lesion. For example, more points may be assigned to a lesion in a critical vessel segment, as opposed to a less critical vessel segment.

The evaluation step 306 may also involve identifying occlusions. For example, computer system 206 may analyze model 220 to identify segments or areas with no intraluminal antegrade flow (TIMI 0) beyond the point of occlusion. Computer system 206 may then assign one or more points based on any identified occlusions. The algorithms may search for drops in contrast down the vessel and detect where the lumen contrast is diminished for a least a minimum distance. In one embodiment, points may be assessed based on the location or identity of the segment containing an occlusion. For example, more points may be assigned to an occlusion in a critical vessel segment, as opposed to a less critical vessel segment. Computer system 206 may also identify, and adjust assessed points based on, the type of occlusion (e.g., blunt stump, bridging collaterals, etc.) Occlusions may be automatically identified by analyzing intensity (Hounsfield unit) changes along the centerline. For example, if the intensity value drops sharply below a certain threshold, then the position along the coronary can be classified as occlusions. The slope of intensity variation and magnitude of intensity may be utilized in this computation.

The evaluation step 306 may also include identifying any bifurcations or trifurcations in the patient's vasculature. A bifurcation may be considered to be a division of a main, parent, branch into two daughter branches of at least 1.5 mm. Bifurcation lesions may involve the proximal main vessel, the distal main vessel and the side branch according to the Medina classification. The smaller of the two daughter branches should be designated as the 'side branch'. In case of the main stem, either the LCX or the LAD may be designated as the side branch depending on their respective calibres. In one embodiment, bifurcations may be scored only for the following segment junctions (based on the numbers assigned above to each coronary artery): 5/6/11, 6/7/9, 7/8/10, 11/13/12a, 13/14/14a, 3/4/16 and 13/14/15. A trifurcation may be considered to be a division of a main-branch into three branches of at least 1.5 mm. In one embodiment, trifurcations may be scored only for the following segment junctions: 3/4/16/16a, 5/6/11/12, 11/12a/12b/13, 6/7/9/9a and 7/8/10/10a. Computer system 206 may then assess points based on the identification of any bifurcation or trifurcation, and the identity or location of any vessel segments containing such features. In one embodiment, computer system 206 may assess points only for segment numbers of the bifurcation/trifurcation that have a diameter stenosis ≥50% in direct contact with the bifurcation/trifurcation. Bifurcation/trifurcations may be identified automatically by counting the number of intersections having a sphere (radius~parent vessel radius) at junctions of constructed coronary centerlines. For example, if there are three intersections, then the junction is bifurcation, whereas if there are four intersections then the junction is trifurcation.

The evaluation step 306 may also involve identifying the existence of ostial disease. Specifically, computer system 206 may process image data from model 220 to identify stenosis that blends into the patient's aorta, or stenosis within some predetermined distance from the ostia, e.g., by using contours. Ostial disease can be automatically identified by evaluating vessel cross-sectional area or analyzing the existence of plaques around the vicinity of ostia locations. Computer system 206 may then assess points based on the identification of any ostial disease, and record the identity or location of any vessel segments containing such disease. Computer system 206 may also adjust the assessed points based on the identified severity or location of any identified ostial disease.

The evaluation step 306 may also involve identifying vessel segments having severe tortuosity. For example, computer system 206 may, based on the identified vessel centerlines discussed above, calculate the curvature of the patient's coronary vessels. Computer system 206 may assess one or more points to vessel segments having a predetermined level of curvature, such as, for example, bends of 90 degrees or more, or three or more bends of 45-90 degrees proximal to the diseased segment. The number of bends can be automatically assessed by computing the angle between tangential vectors of centerline in a sufficiently large interval size (e.g., three times or five times the diameter of vessel). Computer system 206 may then assess points based on the identification of any severe tortuosity, and record the identity or location of any vessel segments containing such severe tortuosity. Computer system 206 may also adjust the assessed points based on the identified severity or location of any identified severe tortuosity.

The evaluation step 306 may also involve computing the lengths of any identified diseased segments. In one embodiment, computer system 206 may analyze model 220 to identify the length of any portion of stenosis that has greater than or equal to 50% reduction in luminal diameter in the projection where the lesion appears to be the longest. Computer system 206 may then assess points based on the identified lengths of any diseased segments, and record the identity or location of any vessel segments containing stenosis of some predetermined threshold length. Computer system 206 may also adjust the assessed points based on the length and/or location of any identified diseased segments.

The evaluation step 306 may also involve computing the dimensions of any identified calcified plaque. In one embodiment, computer system 206 may analyze model 220 to identify the volume and length of any calcified plaque within a stenosis region. Computer system 206 may alternatively or additionally analyze model 220 to identify a surface area bordering identified calcified plaque and adjacent lumen; and/or identify a ratio of such surface area within an identified stenosis region. Computer system 206 may then assess points based on the dimensions of any identified calcified plaque, and record the locations or dimensions of any identified calcified plaque. Computer system 206 may also adjust the assessed points based on the locations or dimensions of any identified calcified plaque. The length of identified calcified plaque can be automatically determined by projecting plaque segmentation onto centerline. The effective cross-sectional area of plaque can be computed by dividing the plaque volume with computed length.

The evaluation step 306 may also involve identifying the existence of thrombus. Specifically, computer system 206 may process image data from model 220 to identify thrombus, e.g., by using contours, contrast, etc. Computer system 206 may then assess points based on the identification of any thrombus, and record the identity or location of any vessel segments containing such thrombus. Computer system 206 may also adjust the assessed points based on the identified severity or location of any identified thrombus. However, in one embodiment, thrombus may be weighted less than other disclosed characteristics 350, or omitted from the cardiovascular score altogether.

The evaluation step 306 may also involve identifying any diffuse disease. In one embodiment, computer system 206 may analyze model 220 to calculate the mean vessel size from contours within or adjacent to an identified stenosis segment. For example, computer system 206 may identify a stenosis segment as exhibiting diffuse disease if greater than 75 percent of a region is less than 2 mm in average diameter. Computer system 206 may then assess points based on the extent of any identified diffuse disease, and record the locations or dimensions of any identified segments having diffuse disease. Computer system 206 may also adjust the assessed points based on the locations or dimensions of any identified segments having diffuse disease.

Thus, evaluation step 306 may include identification and/or computation of one or more characteristics 350, and assessment of one or more points to a patient based on each identification, computation, extent, and/or location of those characteristics 350. Evaluation step 306 may then be followed by generating a patient cardiovascular score based on one or more of the evaluated characteristics and assessed points (step 308). For example, computer system 206 may generate a patient cardiovascular score by executing an algorithm on the characteristics evaluated and/or points assessed in step 306. In one embodiment, the patient cardiovascular score may be generated by summing together all of the points assessed when evaluating the characteristics in step 306. For instance, computer system 206 may add together all of the points assessed for one or more of: (i) identification of left/right coronary dominance; (ii) identification of segments with threshold percentage of stenosis; (iii) identification of occlusions; (iv) identification of bifurcations/trifurcations; (v) identification of ostial disease; (vi) computation of tortuosity; (vii) computation of lengths of diseased segments; (viii) computation of dimensions of calcified plaque; (ix) identification of thrombus; and/or (x) identification of segments with diffuse disease; so as to generate a single cardiovascular score.

In one embodiment, the single generated cardiovascular score may be weighted or normalized such that, if the generated score is less than some predetermined score, then PCI may be the appropriate identified intervention, and if the score is greater than some predetermined score, then CABG may be the appropriate identified intervention. In one embodiment, the generated cardiovascular score may be displayed to a cardiologist or other user through a display device connected to computer system 206. Alternatively or additionally, the generated cardiovascular score may be transmitted to a cardiologist or other third party over the electronic network 200.

In one embodiment, the cardiovascular score generated in step 308 may be weighted or normalized to be compatible with the SYNTAX scoring technique described above. By way of example, the generated cardiovascular score may weighted or normalized such that, if the generated score is less than 34, PCI may be the appropriate identified intervention, and if the score is greater than 34, then CABG may be the appropriate identified intervention.

In one embodiment, the patient cardiovascular score generated in step 308 may be calculated based on a patient's entire coronary vasculature, without regard to each lesion or segment's functional significance on blood flow or pressure. Such a cardiovascular score may be referred to as an "anatomic cardiovascular score." However, as described above, in certain circumstances, it may be advantageous to incorporate in the generated cardiovascular score only points relevant to a functionally significant lesion or characteristic 350. For example, if an area of minor stenosis does not contribute to reduced blood flow or reduced downstream blood pressure, then it may be desirable to avoid counting points associated with such an area into the generated cardiovascular score. Such a cardiovascular score may be referred to as a "functional cardiovascular score."

Accordingly, in one embodiment, method 300 may also include calculating FFR values at a plurality of locations of a patient's coronary vasculature (step 312). Method 300 may also then include generating a patient cardiovascular score based on evaluated characteristics for a subset of locations having predetermined threshold level of FFR values (step 310), i.e., a "functional cardiovascular score." For example, in one embodiment, at least one FFR value may be calculated for each segment of a patient's coronary vasculature. The patient cardiovascular score may be calculated based only on points assessed to vessel segments that have an FFR value below some predetermined threshold value. In an alternative embodiment, functional values other than FFR values may be used to perform scoring only on functionally significant vessel segments. For example, myocardial perfusion, flow rates, etc. may be considered and used to screen vessel segments whose characteristics may be incorporated into the cardiovascular score. In one embodiment, instead of generating a cardiovascular score only based on segments having a threshold functional significance, an anatomic (i.e., complete vasculature) score may be modified by removing from the existing calculation those segments not meeting the threshold functional significance.

In one embodiment, the patient cardiovascular score may be calculated based only on points assessed to vessel segments that have an FFR value below 0.9. In one embodiment, the patient cardiovascular score may be calculated based only on points assessed to vessel segments that have an FFR value below 0.8. In one embodiment, the patient cardiovascular score may be calculated based only on points assessed to vessel segments that have an FFR value below 0.7. Thus, the patient cardiovascular score may be calculated based only on vessel segments that actually contribute to dysfunction of the patient's coronary vasculature. As described above, any of such patient cardiovascular scores may be referred to as a "functional cardiovascular score."

It will be appreciated that FFR calculation step 312 may be performed according to any known methods, but preferably using noninvasive techniques. For instance, in one embodiment, FFR calculation step 312 may be performed according to the systems and methods for such calculations described in U.S. patent application Ser. No. 13/013,561, filed Jan. 25, 2011, and entitled "Method and System for Patient-Specific Modeling of Blood Flow," which is assigned to the assignee of the present application and which is hereby incorporated by reference in its entirety. By way of example, FFR calculation step 312 may be performed according to the system and method described below with respect to FIGS. 4 and 5.

Figure 4:
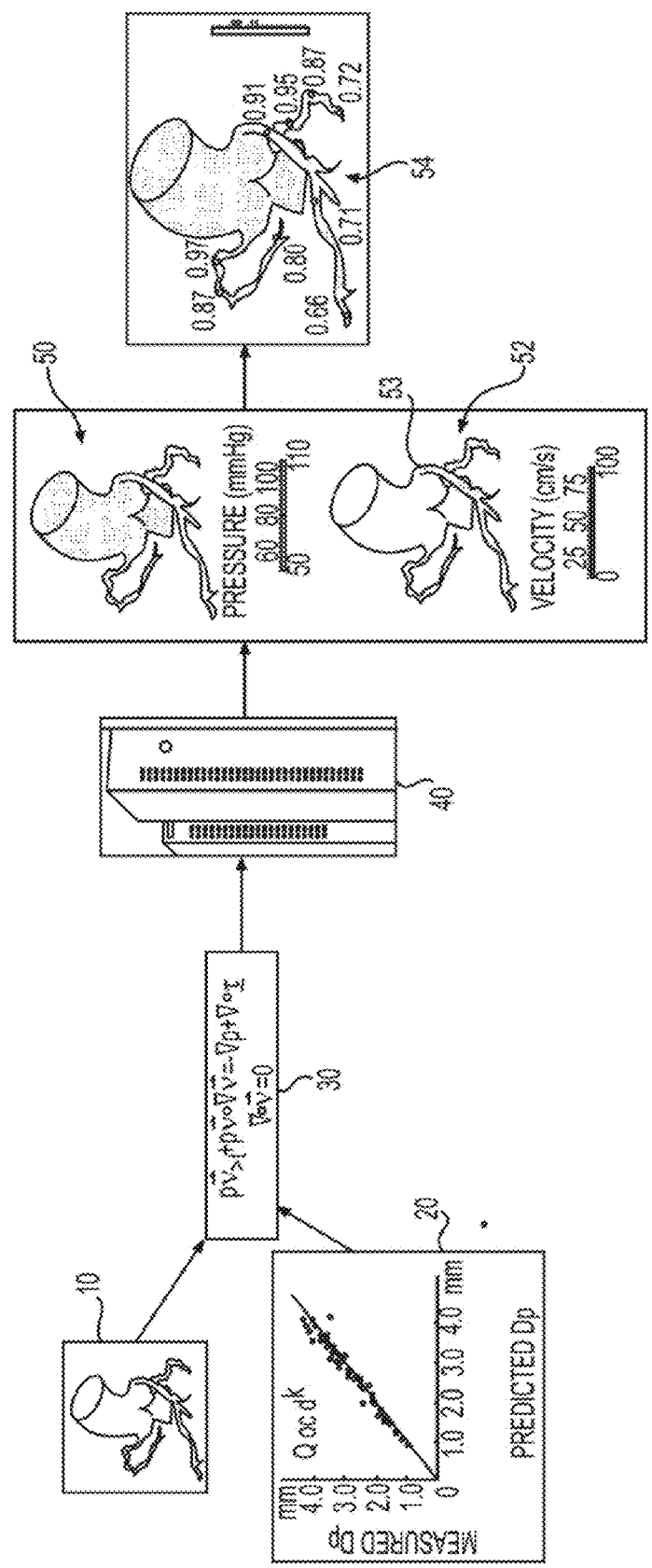
FIG. 4 is a schematic diagram of a system for providing various information relating to coronary blood flow in a specific patient, according to embodiments of the present disclosure.

FIG. 4 shows aspects of a system for providing various information (e.g., FFR) relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, a plurality of equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 may be solvable to determine information (e.g., pressure, velocity, FFR, etc.) about the coronary blood flow in the patient's anatomy at various points in the anatomy represented by the model 10.

The equations 30 may be solved using a computer 40. Based on the solved equations, the computer 40 may output one or more images or simulations indicating information relating to the blood flow in the patient's anatomy represented by the model 10. For example, the image(s) may include a simulated blood pressure model 50, a simulated blood flow or velocity model 52, a computed FFR (cFFR) model 54, etc., as will be described in further detail below. The simulated blood pressure model 50, the simulated blood flow model 52, and the cFFR model 54 provide information regarding the respective pressure, velocity, and cFFR at various locations along three dimensions in the patient's anatomy represented by the model 10. cFFR may be calculated as the ratio of the blood pressure at a particular location in the model 10 divided by the blood pressure in the aorta, e.g., at the inflow boundary of the model 10, under conditions of maximally increased coronary blood flow, e.g., conventionally induced by intravenous administration of adenosine.

In an exemplary embodiment, the computer 40 may include one or more non-transitory computer-readable storage devices that store instructions that, when executed by a processor, computer system, etc., may perform any of the actions described herein for providing various information relating to blood flow in the patient. The computer 40 may include a desktop or portable computer, a workstation, a server, a personal digital assistant, or any other computer system. The computer 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer 40 to a network, a display adapter for connecting the computer 40 to a display, etc. For example, the display may be used to display the three-dimensional model 10 and/or any images generated by solving the equations 30, such as the simulated blood pressure model 50, the simulated blood flow model 52, and/or the cFFR model 54.

Figure 5:
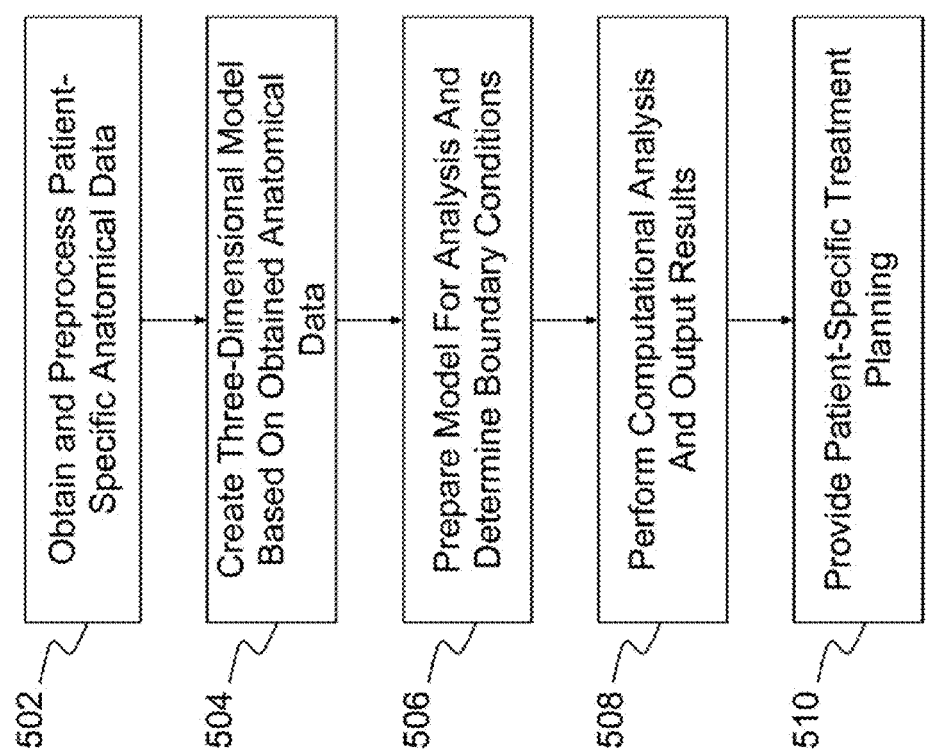
FIG. 5 is a block diagram of an exemplary method for providing various information relating to coronary blood flow in a specific patient, according to embodiments of the present disclosure.

FIG. 5 shows aspects of a method for providing various information relating to blood flow in a specific patient, according to another exemplary embodiment. The method may include obtaining patient-specific anatomical data, such as information regarding the patient's anatomy (e.g., at least a portion of the aorta and a proximal portion of the main coronary arteries (and the branches extending therefrom) connected to the aorta), and preprocessing the data (step 502). The patient-specific anatomical data may be obtained noninvasively, e.g., by CCTA.

A three-dimensional model of the patient's anatomy may be created based on the obtained anatomical data (step 504). For example, the three-dimensional model may be the three-dimensional model 10 (FIG. 4) or three-dimensional model 220 (FIG. 1) of the patient's anatomy, generated as discussed above with respect to FIG. 3.

The three-dimensional model may be prepared for analysis and boundary conditions may be determined (step 506). For example, the three-dimensional model 10 of the patient's anatomy described above in connection with FIG. 4 may be trimmed and discretized into a volumetric mesh, e.g., a finite element or finite volume mesh. The volumetric mesh may be used to generate the equations 30 described above in connection with FIG. 4.

Boundary conditions may also be assigned and incorporated into the equations 30 described above in connection with FIG. 4. The boundary conditions provide information about the three-dimensional model 10 at its boundaries, e.g., inflow boundaries, outflow boundaries, vessel wall boundaries, etc. The inflow boundaries may include the boundaries through which flow is directed into the anatomy of the three-dimensional model, such as at an end of the aorta near the aortic root. Each inflow boundary may be assigned, e.g., with a prescribed value or field for velocity, flow rate, pressure, or other characteristic, by coupling a heart model and/or a lumped parameter model to the boundary, etc. The outflow boundaries may include the boundaries through which flow is directed outward from the anatomy of the three-dimensional model, such as at an end of the aorta near the aortic arch, and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the three-dimensional model 10.

The computational analysis may be performed using the prepared three-dimensional model and the determined boundary conditions (step 508) to determine blood flow information for the patient. For example, the computational analysis may be performed with the equations 30 and using the computer 40 described above in connection with FIG. 4 to produce the images described above in connection with FIG. 4, such as the simulated blood pressure model 50, the simulated blood flow model 52, and/or the cFFR model 54.

The method may also include providing patient-specific treatment options using the results (step 510). For example, the three-dimensional model 10 created in step 504 and/or the boundary conditions assigned in step 506 may be adjusted to model one or more treatments, e.g., placing a coronary stent in one of the coronary arteries represented in the three-dimensional model 10 or other treatment options. Then, the computational analysis may be performed as described above in step 508 in order to produce new images, such as updated versions of the blood pressure model 50, the blood flow model 52, and/or the cFFR model 54. These new images may be used to determine a change in blood flow velocity and pressure if the treatment option(s) are adopted.

The systems and methods disclosed herein may be incorporated into a software tool accessed by physicians to provide a noninvasive means to quantify blood flow in the coronary arteries and to assess the functional significance of coronary artery disease. In particular, the calculated FFR values, as reflected in the cFFR model 54, may be incorporated into the step of generating a functional cardiovascular score. Specifically, as discussed above with respect to step 310 of method 300, a cardiovascular score may be generated based on evaluated characteristics and assessed points for a subset of coronary segments having FFR values with a predetermined functional range. Accordingly, the resulting cardiovascular score may be more relevant to actual function or dysfunction of various segments of a patient's coronary vasculature, and more likely to be indicative of a desirable intervention technique (e.g., PCI vs. CABG).

In addition to calculating a functional cardiovascular score, physicians may use the system to predict the effect of medical, interventional, and/or surgical treatments on coronary artery blood flow. The system may prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The software tool may be interactive to enable physicians to develop optimal personalized therapies for patients.

For example, the system may be incorporated at least partially into a computer system, e.g., the computer 40 shown in FIG. 4 used by a physician or other user. The computer system may receive data obtained noninvasively from the patient (e.g., data used to create the three-dimensional model 10, data used to apply boundary conditions or perform the computational analysis, etc.). For example, the data may be input by the physician or may be received from another source capable of accessing and providing such data, such as a radiology or other medical lab. The data may be transmitted via a network or other system for communicating the data, or directly into the computer system. The software tool may use the data to produce and display the three-dimensional model 10 or other models/meshes and/or any simulations or other results determined by solving the equations 30 described above in connection with FIG. 4, such as the simulated blood pressure model 50, the simulated blood flow model 52, and/or the cFFR model 54. Thus, the system may perform steps 302-312 and/or steps 502-510. In step 502, the physician may provide further inputs to the computer system to select possible treatment options, and the computer system may display to the physician new simulations based on the selected possible treatment options. Further, each of steps 302-312 and 502-510 shown in FIGS. 3 and 5 may be performed using separate computer systems, software packages, or modules.

Alternatively, the system may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the data obtained noninvasively from the patient may be provided to the service provider, and the service provider may use the data to produce the three-dimensional model 10 or other models/meshes and/or any simulations or other results determined by solving the equations 30 described above in connection with FIG. 4, such as the simulated blood pressure model 50, the simulated blood flow model 52, and/or the cFFR model 54. Then, the web-based service may transmit information relating to the three-dimensional model 10 or other models/meshes and/or the simulations so that the three-dimensional model 10 and/or the simulations may be displayed to the physician on the physician's computer system. Thus, the web-based service may perform steps 302-312 and/or steps 502-510 and any other steps described above for providing patient-specific information. In step 502, the physician may provide further inputs, e.g., to select possible treatment options or make other adjustments to the computational analysis, and the inputs may be transmitted to the computer system operated by the service provider (e.g., via the web portal). The web-based service may produce new simulations or other results based on the selected possible treatment options, and may communicate information relating to the new simulations back to the physician so that the new simulations may be displayed to the physician.

One or more of the steps described herein may be performed by one or more human operators (e.g., a cardiologist or other physician, the patient, an employee of the service provider providing the web-based service or other service provided by a third party, other user, etc.), or one or more computer systems used by such human operator(s), such as a desktop or portable computer, a workstation, a server, a personal digital assistant, etc. The computer system(s) may be connected via a network or other method of communicating data.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

Various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for automatically generating a cardiovascular score for a patient, the method comprising:
   receiving, using at least one computer system, non-invasively obtained patient-specific image data regarding a geometry of one or more coronary arteries of the patient;
   creating, using the at least one computer system, a three-dimensional model representing a plurality of portions of the one or more coronary arteries of the patient using the patient-specific image data;
   automatically determining, using the at least one computer system, a value of a blood flow property for each of the plurality of portions of the one or more coronary arteries using the three-dimensional model;
   automatically determining, using the at least one computer system, a subset of the portions of the one or more coronary arteries having values of the blood flow property meeting a predetermined threshold of functional significance;
   automatically evaluating, using the at least one computer system, multiple characteristics of the subset of the portions of the one or more coronary arteries, wherein at least one of the multiple characteristics is selected from the group of left/right dominance, a total occlusion, a presence of an ostial disease, a tortuosity value, a length of a diseased vessel segment, one or more dimensions of calcified plaque, a thrombus, and a presence of a diffuse disease, and wherein automatically evaluating the multiple characteristics comprises automatically generating a numerical measurement of at least part of each characteristic;
   automatically assigning, using the at least one computer system, a point value to each of the multiple characteristics based on the evaluation and generated numerical measurement of each characteristic; and
   for the subset of the portions of the one or more coronary arteries meeting the predetermined threshold of functional significance, automatically executing an algorithm using the assigned point values to generate a cardiovascular score.

2. A method as in claim 1, wherein receiving the patient-specific data comprises receiving data generated from a noninvasive imaging modality.

3. A method as in claim 1, wherein each of the multiple characteristics is selected from the group consisting of left/right dominance, identification of segment(s) of coronary arteries with disease, presence of total occlusions, presence of bifurcations and trifurcations, presence of ostial disease, computation of tortuosity, computation of length of diseased segment(s), computation of dimensions of calcified plaque, identification of thrombus, and presence of diffuse disease.

4. A method as in claim 1, wherein the blood flow property includes one or more fractional flow reserve values for at least the subset of the coronary arteries.

5. A method as in claim 4, wherein the predetermined threshold value is a fractional flow reserve value between 0.7 and 0.9.

6. A method as in claim 1, wherein the method is performed without receiving any additional input, other than the patient-specific data regarding the geometry.

7. A computer-implemented method for generating a cardiovascular score for a patient, the method comprising:
   receiving, using at least one computer system, non-invasively obtained patient-specific image data regarding a geometry of one or more coronary arteries of the patient;
   creating, using the at least one computer system, a three-dimensional model representing a plurality of portions of the one or more coronary arteries of the patient using the patient-specific image data;
   automatically determining, using the at least one computer system, a value of a blood flow property for each of a plurality of portions of the one or more coronary arteries using the three-dimensional model;
   automatically determining, using the at least one computer system and the three-dimensional model, a subset of the portions of the one or more coronary arteries having values of the blood flow property meeting a predetermined threshold of functional significance;

for the subset of the portions of the one or more coronary arteries meeting the predetermined threshold of functional significance, automatically assigning numerical values to each of a plurality of characteristics of the subset of the portions of the one or more coronary arteries meeting the predetermined threshold of functional significance;
and
for the subset of the portions of the one or more coronary arteries meeting the predetermined threshold of functional significance, automatically executing an algorithm using the at least one computer system and the assigned numerical values to generate cardiovascular score.

8. A method as in claim 7, wherein receiving the patient-specific data comprises receiving data generated from a noninvasive imaging modality.

9. A method as in claim 7, wherein the characteristics are selected from the group consisting of left/right dominance, identification of segment(s) of coronary arteries with disease, presence of total occlusions, presence of bifurcations and trifurcations, presence of ostial disease, computation of tortuosity, computation of length of diseased segment(s), computation of dimensions of calcified plaque, identification of thrombus, and presence of diffuse disease.

10. A method as in claim 7, wherein generating the cardiovascular score includes generating a fractional flow reserve value for at least one of the coronary arteries.

11. A method as in claim 10, wherein the predetermined threshold value is a fractional flow reserve value between 0.7 and 0.9.

12. A method as in claim 7, wherein the method is performed without receiving any additional input, other than the patient-specific data regarding the geometry.

13. A method for providing a cardiovascular score for a patient, the method comprising:
receiving, using at least one computer system, non-invasively obtained patient-specific image data regarding a geometry of one or more coronary arteries of the patient;
creating, using the at least one computer system, a three-dimensional model representing one or more coronary arteries based on the non-invasively obtained patient-specific image data;
automatically calculating, using the at least one computer system, fractional flow reserve values at a plurality of locations of the one or more coronary arteries using the three-dimensional model;
automatically determining, using the at least one computer system a subset of the portions of the one or more coronary arteries having values of the fractional flow reserve meeting a predetermined threshold of functional significance;
automatically evaluating, using the at least one computer system, multiple characteristics of the subset of the portions of the one or more coronary arteries represented by the three-dimensional model by identifying one or more geometrical features of the subset of portions extracted from the patient-specific image data;
automatically assigning, using the at least one computer system, a numerical value to each of the multiple characteristics based on the evaluation; and
automatically executing an algorithm, using the at least one computer system, to calculate a functional cardiovascular score for the determined subset of the portions of the one or more coronary arteries having a fractional flow reserve value meeting the predetermined threshold of functional significance.

14. A method as in claim 13, wherein each of the multiple characteristics is selected from the group consisting of left/right dominance, identification of segment(s) of coronary arteries with disease, presence of total occlusions, presence of bifurcations and trifurcations, presence of ostial disease, computation of tortuosity, computation of length of diseased segment(s), computation of dimensions of calcified plaque, identification of thrombus, and presence of diffuse disease.

15. A method as in claim 13, wherein the predetermined threshold value is one of 0.7, 0.8, and 0.9.

16. A method as in claim 13, wherein the fractional flow reserve values are calculated based on the three-dimensional model and one of a reduced-order model, a physics-based model, and a lumped-parameter model of blood flow.

17. A method as in claim 1, wherein the multiple characteristics are evaluated using the three-dimensional model.

18. The method of claim 17, wherein the multiple characteristics are evaluated based on the computer system analyzing one or more of: image contrast, image contours, image gradients, post-processed images, image intensities, shape, and volumetric mesh of the three-dimensional model.

19. A method as in claim 7, wherein the multiple characteristics meeting the predetermined threshold of functional significance are assigned numerical values using the three-dimensional model.

20. The method of claim 19, wherein the multiple characteristics are assigned numerical values based on the computer system analyzing one or more of: image contrast, image contours, image gradients, post-processed images, image intensities, shape, and volumetric mesh of the three-dimensional model.

* * * * *